United States Patent [19]

Seiler

[11] 4,143,143

[45] Mar. 6, 1979

[54] SUBSTITUTED IMIDAZO[5,1-A]ISOQUINOLINES

[75] Inventor: Max-Peter Seiler, Basel, Switzerland

[73] Assignee: Sandoz Ltd., Basel, Switzerland

[21] Appl. No.: 835,986

[22] Filed: Sep. 23, 1977

[30] Foreign Application Priority Data

Sep. 29, 1976 [CH] Switzerland ............... 12302/76

[51] Int. Cl.² .................... C07D 471/14; A61K 31/47
[52] U.S. Cl. ............................... 424/258; 260/562 N; 546/84; 546/77
[58] Field of Search ................. 260/288 CF; 424/258

[56] References Cited

U.S. PATENT DOCUMENTS

| | | | |
|---|---|---|---|
| 3,557,120 | 1/1971 | Archer et al. | 260/288 CF |
| 3,804,833 | 4/1974 | Stähle et al. | 548/315 X |
| 3,917,610 | 11/1975 | Takacs | 260/288 CF |
| 3,937,717 | 2/1976 | Stähle et al. | 548/316 |

FOREIGN PATENT DOCUMENTS

| | | | |
|---|---|---|---|
| 2332860 | 3/1974 | Fed. Rep. of Germany. | |
| 1542161 | 10/1968 | France | 548/315 |
| 1229993 | 4/1971 | United Kingdom | 548/315 |

Primary Examiner—Donald G. Daus
Assistant Examiner—Diana G. Rivers
Attorney, Agent, or Firm—Gerald D. Sharkin; Robert S. Honor; Timothy G. Rothwell

[57] ABSTRACT

Compounds of formula I,

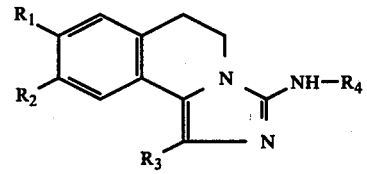

wherein either $R_1$ is hydroxy or alkoxy of 1 to 4 carbon atoms, and
$R_2$ is hydrogen, hydroxy or alkoxy of 1 to 4 carbon atoms,
or $R_1$ and $R_2$, together, are methylenedioxy,
$R_3$ is hydrogen or alkyl of 1 to 4 carbon atoms, and
$R_4$ is phenyl or phenyl substituted by 1, 2 or 3 substituents independently chosen from halogen, hydroxy, nitro or alkyl($C_{1-4}$) haloalkyl($C_{1-4}$), or alkoxy ($C_{1-4}$), are useful as anti-arrhythmic agents.

14 Claims, No Drawings

SUBSTITUTED IMIDAZO[5,1-A]ISOQUINOLINES

The present invention relates to imidazoisoquinolines.

The present invention provides compounds of formula I,

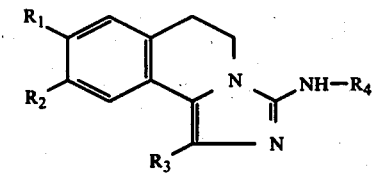

wherein either $R_1$ is hydroxy or alkoxy of 1 to 4 carbon atoms, and $R_2$ is hydrogen, hydroxy or alkoxy of 1 to 4 carbon atoms, or $R_1$ and $R_2$, together, are methylenedioxy, $R_3$ is hydrogen or alkyl of 1 to 4 carbon atoms, $R_4$ is phenyl or phenyl substituted by 1, 2 or 3 substituents independently chosen from halogen, hydroxy, nitro or alkyl($C_{1-4}$) haloalkyl($C_{1-4}$) or alkoxy($C_{1-4}$).

Halogen or halo refers to bromine, chlorine, fluorine or iodine, preferably bromine, chlorine or fluorine. Any alkyl, alkoxy or haloalkyl moiety has preferably 1 to 2 carbon atoms or, especially 1 carbon atom. Haloalkyl refers to mono-, di- or tri-haloalkyl, especially trifluoromethyl.

$R_1$ and $R_2$ are preferably either both independently alkoxy or together methylenedioxy and are especially both independently alkoxy.

$R_3$ is preferably alkyl. Compounds wherein $R_4$ is substituted phenyl are preferred to those wherein $R_4$ is phenyl. Preferably two substituents are present on the phenyl ring. Preferably at least one substituent is present ortho to the -NH- moiety. Preferred substituents are haloalkyl groups, or especially alkyl groups.

The present invention provides a process for the preparation of a compound of formula I, as defined above, which comprises reacting a compound of formula II,

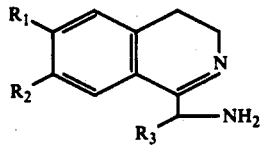

wherein $R_1$, $R_2$ and $R_3$ are as defined above, with a compound of formula III,

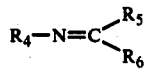

wherein $R_4$ is as defined above, and $R_5$ and $R_6$ are leaving groups.

The process may be effected in conventional manner for the production of analogous imidazole compounds by condensation of diamines.

Dimethylformamide or 1,2-dimethoxyethane may be used as solvent. Suitable reaction temperatures may be from 30° to 100° C. Preferably $R_5$ and $R_6$ are each chlorine.

A compound of formula II may be produced by treating a compound of formula IV,

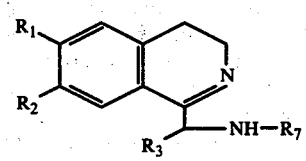

wherein $R_1$ to $R_3$ are as defined above, and $R_7$ is carbobenzoxy, with hydrogen bromide in acetic acid.

A compound of formula IV may be produced by reacting a compound of formula V,

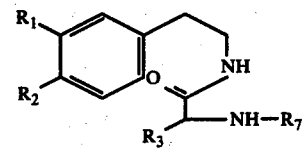

wherein $R_1$ to $R_3$ and $R_7$ are as defined above, with phosphorus oxychloride.

A compound of formula V may be produced by condensing a compound of formula VI, $$HOOC.CH(R_3).NHR_7 \qquad VI$$

wherein $R_3$ and $R_7$ are as defined above, with an appropriate phenylethylamine using methods known in peptide synthesis.

Insofar as the production of any particular starting material is not particularly described, this is known or may be produced in conventional manner.

Acid addition salt forms may be prepared from the free base forms of compounds of formula I in conventional manner and vice versa.

In the following Examples all temperatures are in degrees Centigrade and are uncorrected.

EXAMPLE 1

5,6-dihydro-8,9-dimethoxy-1-methyl-3-(2,6-dimethylphenylamino)imidazo[5,1-a]isoquinoline 2.9 g 2,6-dimethylphenylisocyanide dichloride is added to a suspension of 5 g of 1-(1-aminoethyl)-3,4-dihydro-6,7-dimethoxyisoquinoline dihydrobromide in 100 ml dimethylformamide. 3.6 g of anhydrous potassium carbonate are then added. The suspension is stirred and warmed at 60° for 6 hours. The potassium carbonate is filtered off and washed with dimethylformamide. The washings and filtrate are concentrated in a vacuum, and the residue is chromatographed on silicagel using $CHCl_3/CH_3OH$ (95:5) as eluant to give the title compound as the free base; M.Pt. 234°-236°.

If desired, the isoquinoline starting material may be used in free base form and the reaction effected in the absence of potassium carbonate to afford directly the hydrochloride form of the end product which generally crystallizes out of the reaction mixture.

The isoquinoline starting material may be prepared as follows:

(a) 138.8 g dicyclohexylcarbodiimide is added to a 0° solution of 150 g DL-carbobenzoxyalanine and 116.3 g N-hydroxysuccinimide in 1 liter acetonitrile. After the mixture has been stirred for 2 hours at room temperature, the mixture is filtered and treated with 122.5 g 2-(3,4-dimethoxyphenyl)ethylamine in 100 ml acetonitrile. The resultant mixture is stirred for 20 hours and then concentrated. 2-carbobenzoxyamino-N-[2-(3,4-dimethoxyphenyl)ethyl]propionic acid amide (M.Pt. 122°–123°), crystallizes out.

(b) 145 ml of phosphorus oxychloride is added to a suspension of 145 g of the above acid amide in 1.1 liters benzene. The suspension is refluxed for 2 hours, allowed to cool and then concentrated to an oil. The oil is taken up in ethyl acetate and extracted with 1 N HCl. The aqueous phase is adjusted to pH 8 with 4 N NaOH and extracted with ethyl acetate. The extracts are dried with sodium sulphate, and concentrated to an oil which crystallizes on standing. Scratching of the crystallate, washing with petroleum ether and drying gives 1-(1-carbobenzoxyaminoethyl)-3,4-dihydro-6,7-dimethoxyisoquinoline. M.Pt. 84°–86°.

(c) 40 g 1-(1-carbobenzoxyaminoethyl)-3,4-dihydro-6,7-dimethoxyisoquinoline are dissolved in 450 ml 40% HBr/acetic acid. The mixture is maintained at room temperature for 1 hour and then concentrated in a vacuum to give a crystalline residue of 1-(1-aminoethyl)-3,4-dihydro-6,7-dimethoxyisoquinoline dihydrobromide which is washed with ether before further use (M.Pt. 234°–235°).

In analogous manner to that described in Example 1, there are produced the following compounds of formula I, wherein $R_1$ and $R_2$ are both methoxy, $R_3$ is methyl, and $R_4$ is as defined below

| Ex. No. | $R_4$ | M.Pt. |
|---|---|---|
| 2 | 2,6—di—Cl—$C_6H_3$— | 287°–289° [1] |
| 3 | 3—F—$C_6H_4$— | 212°–214° [1] |
| 4 | 3—Cl—$C_6H_4$— | 235°–238° [2] |
| 5 | $C_6H_5$— | 188°–190° [1] |
| 6 | 4—$CH_3O$—$C_6H_4$— | 161°–163° [3] |
| 7 | 4—$NO_2$—$C_6H_4$— | 245°–246° [4] |
| 8 | 2,3—diCl—$C_6H_3$— | 271°–273° [2] |
| 9 | 3—$CF_3$—$C_6H_4$— | 245°–247° [2][2] |
| 10 | 3,5—di—Cl—$C_6H_3$— | 308°–310° [2] |
| 11 | 3,4—di—Cl—$C_6H_3$— | 266°–268° [2] |

[1] Free base
[2] Hydrocholoride
[3] Hydrogen fumarate
[4] bis[base] fumarate

In analogous manner to that described in Example 1, the following compounds of formula I may be obtained, wherein:-

| $R_1$ | $R_2$ | $R_3$ | $R_4$ |
|---|---|---|---|
| OH | OH | H | 4—$C_2H_5O$—$C_6H_4$— |
| OH | H | H | 4—$C_2H_5O$—$C_6H_4$— |
| —O—$CH_2$—O— | | H | 2,3,5—tri—OH—$C_6H_2$— |

The compounds of formula I are useful because they possess pharmacological activity in animals. In particular, the compounds of formula I are useful as antiarrhythmic agents, e.g. for the treatment of heart rhythm disorders as indicated by an inhibition of the chloroform-induced arrhythmia in mice according to the principles of J. W. Lawson, J. Pharmac. exp. Ther. 160, 22-31 (1968) on administration of from about 5 to about 50 mg/kg p.o.

For the above mentioned use the dosage will, of course, vary depending on the compound employed, mode of administration and therapy desired. However, in general, satisfactory results are obtained when administered at a daily dosage of from 0.05 mg to about 50 mg per kg animal body weight, conveniently given in divided doses 2 to 4 times a day or in sustained release form. For the larger mammal, the total daily dosage is in the range from about 5 to about 100 mg, and dosage forms suitable for oral administration comprise from about 1 mg to about 50 mg of the compounds admixed with a solid or liquid pharmaceutical carrier or diluent.

The Example 1 compound has been found to be a particularly effective arrhythmic agent in the rat at from 5 to 50 mg/kg p.o.

The compounds of formula I may be administered in pharmaceutically acceptable acid addition salt form. Such salt forms have the same order of activity as the free base forms. The present invention provides a pharmaceutical composition comprising a compound of formula I in free base form or in pharmaceutically acceptable acid addition salt form in association with a pharmaceutical carrier or diluent. Such compositions may be prepared in conventional manner so as to be, for example, a solution, a capsule or a tablet.

I claim:

1. A compound of formula I,

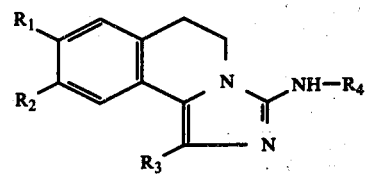

wherein either $R_1$ is hydroxy or alkoxy of 1 to 4 carbon atoms, and
$R_2$ is hydrogen, hydroxy or alkoxy of 1 to 4 carbon atoms,
or $R_1$ and $R_2$, together, are methylenedioxy,
$R_3$ is hydrogen or alkyl of 1 to 4 carbon atoms, and
$R_4$ is phenyl or phenyl substituted by 1, 2 or 3 substituents independently chosen from halogen, hydroxy, nitro or alkyl($C_{1-4}$) haloalkyl($C_{1-4}$) or alkoxy($C_{1-4}$),
in free base form or in pharmaceutically acceptable acid addition salt form.

2. A pharmaceutical composition having antiarrhythmic properties comprising a compound of claim 1, in association with a pharmaceutical carrier or diluent.

3. A method of treating arrhythmic disorders in animals which comprises administering a therapeutically effective amount of a compound of claim 1 to an animal in need of such treatment.

4. The compound of claim 1 which is 5,6-dihydro-8,9-dimethoxy-1-methyl-3-(2,6-dimethylphenylamino)imidazo [5,1-a]isoquinoline.

5. The compound of claim 1 wherein $R_1$ and $R_2$ are methoxy, $R_3$ is methyl and $R_4$ is 2,6-dichlorophenyl.

6. The compound of claim 1 wherein $R_1$ and $R_2$ are methoxy, $R_3$ is methyl and $R_4$ is 4-fluorophenyl.

7. The compound of claim 1 wherein $R_1$ and $R_2$ are methoxy, $R_3$ is methyl and $R_4$ is 3-chlorophenyl.

8. The compound of claim 1 wherein $R_1$ and $R_2$ are methoxy, $R_3$ is methyl and $R_4$ is phenyl.

9. The compound of claim 1 wherein $R_1$ and $R_2$ are methoxy, $R_3$ is methyl and $R_4$ is 4-methoxyphenyl.

10. The compound of claim 1, wherein $R_1$ and $R_2$ are methoxy, $R_3$ is methyl and $R_4$ is 4-nitrophenyl.

11. The compound of claim 1, wherein $R_1$ and $R_2$ are methoxy, $R_3$ is methyl and $R_4$ is 2,3-dichlorophenyl.

12. The compound of claim 1, wherein $R_1$ and $R_2$ are methoxy, $R_3$ is methyl and $R_4$ is 3-trifluoromethylphenyl.

13. The compound of claim 1 wherein $R_1$ and $R_2$ are methoxy, $R_3$ is methyl and $R_4$ is 3,5-dichlorophenyl.

14. The compound of claim 1 wherein $R_1$ and $R_2$ are methoxy, $R_3$ is methyl and $R_4$ is 3,4-dichlorophenyl.

* * * * *

UNITED STATES PATENT AND TRADEMARK OFFICE
CERTIFICATE OF CORRECTION

PATENT NO. : 4,143,143
DATED : Mar. 6, 1979
INVENTOR(S) : Max-Peter Seiler

It is certified that error appears in the above-identified patent and that said Letters Patent are hereby corrected as shown below:

Col. 3, line 42, in the table, the third column of #9 should read -- $245° - 247°\ ^2$ --.

Col. 3, line 40, in the table, the second column of #7 should read -- $4\text{-NO}_2\text{-C}_6\text{H}_4\text{-}$ --.

Signed and Sealed this

Seventeenth Day of July 1979

[SEAL]

Attest:

Attesting Officer

LUTRELLE F. PARKER
Acting Commissioner of Patents and Trademarks